United States Patent [19]

Matsushita

[11] Patent Number: 4,610,679
[45] Date of Patent: Sep. 9, 1986

[54] BEDSORE-FREE DIAPER

[76] Inventor: Masao Matsushita, 1-11-8 Kohama Nishi, Suminoe-ku, Osaka, Japan

[21] Appl. No.: 782,862

[22] Filed: Oct. 2, 1985

[30] Foreign Application Priority Data

Mar. 15, 1985 [JP] Japan .............................. 5037669[U]

[51] Int. Cl.$^4$ ............................................. A61F 13/16
[52] U.S. Cl. ................................. 604/369; 604/385 R
[58] Field of Search ............... 604/369, 358, 366, 370, 604/385.1

[56] References Cited

U.S. PATENT DOCUMENTS

| | | | |
|---|---|---|---|
| 3,461,872 | 8/1969 | McConnell et al. ................ | 604/369 |
| 3,468,311 | 9/1969 | Gallagher ....................... | 604/369 X |
| 3,816,227 | 6/1974 | Schaar ........................... | 604/369 X |
| 4,029,100 | 6/1977 | Karami ........................... | 604/369 |

*Primary Examiner*—John D. Yasko
*Attorney, Agent, or Firm*—Koda and Androlia

[57] ABSTRACT

A bedsore-free diaper folded portions for preventing lateral leak of human waste out of the diaper, a water absorbent cushion mat including a plurality of pneumatically distended portions provided independently of each other inside the diaper in such a manner that the distended portions face a side in contact with human body so as to correspond wth the lumosacral region of the human body inside the diaper and a guide mark provided inside the diaper on substantially a center line in the longitudinal direction of the direction at a specified interval from the cushion mat to provide an indication mark by which the user can precisely apply the cushion mat to the lumbosacral region.

8 Claims, 6 Drawing Figures

BEDSORE-FREE DIAPER

BACKGROUND OF THE INVENTION

1. Field of the Invention

This invention relates to a throwaway diaper and more particularly to a throwaway diaper designed to prevent bedsores and lateral leak of human waste out of the diaper.

2. Prior Art

Patients long confined to bed suffer greatly from bedsores and the effects produced by the bedsores on the patients are in no way small. In addition, the bedsores constitute a cause of spiritual and physical burden on those who tend the patients. Because the patients' weight rest on their skin over a certain region for a long time, they are caused by necrosis of the skin due to the incomplete circulation of the blood on the periphery of the skin and also to the obstruction of air permeation. The regions wherein bedsores often form are the lumbosacral region (region extending from the lumbar vertebra to the sacrum sacral vertebra), scapular region, nape region, elbow region, heel region, etc., and particularly a degree of body weight resting on the lumbosacral region is great and the reduction of air permeability caused by dampness due to human waste is also very great in the lumbosacral region, which fact tends to involve growth and contamination of bacteria. Under the circumstances it was general practice to prevent the skin from getting moist by perspiration and excretion by applying a diaper consisting in combination of a multilayered water absorbent mat and a waterproof sheet to the region ranging from the lumbosacral region to the crotch where bedsores most often form.

But a combination of such water-absorptive mat and waterproof sheet not only does not prevent the entire surface of the skin in contact with bedding from being placed under pressure by body weight but also lays a limit on the water-absorbability by the bedding of sweat and human waste, and accordingly, such a diaper must be repeatedly replaced by a new one, and if otherwise, it often formed a cause of progress in bedsores due to a reduction in air permeabilitly. Further, no measure has been taken for the prevention of lateral leak of human waste out of the diaper and for a guide mark for adequately putting on a diaper.

SUMMARY OF THE INVENTION

This invention is directed toward the solution of the problems described above and has for its object the provision of an improved bedsore-free diaper which prevents lateral leak of human waste out of the diaper. This object is attained by the construction characterized in that, in a diaper formed of water absorbent sheets laid in layers, the bedsore-free diaper comprises folded portions for the prevention of lateral leak of human waste out of the diaper, the folded portions being disposed at both sides of the diaper with the portions directed upwardly; a water absorbent cushion mat including a plurality of pneumatically distended portions, the portions being provided independently of each other inside the diaper in such a manner that the distended portions face the side in contact with the lumbosacral region of the human body inside the diaper; and a guide mark provided inside the diaper on substantially a center line in the longitudinal direction of the diaper at specified interval from the cushion mat, the mark being intended to provide the indication mark by which the user can precisely apply the cushion mat portion to the lumbosacral region.

The invention will now be described in detail with reference to the accompanying drawings.

DETAILED DESCRIPTION OF THE INVENTION

Figure 1:
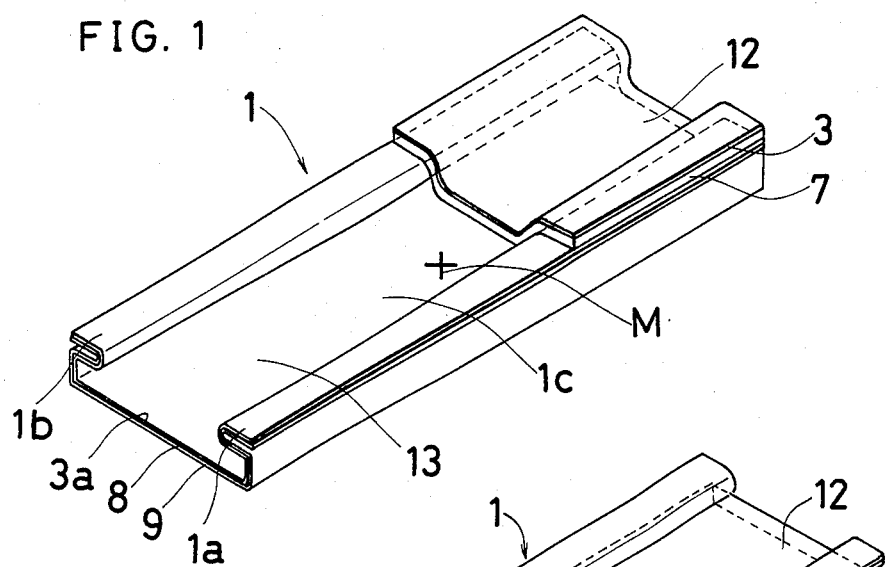
FIG. 1 is a perspective view showing a bedsore-free diaper of one embodiment of the invention.

In FIG. 1 showing a first embodiment of the invention, a bedsore-free diaper 1 comprises a rectangular base of the multilayered construction wherein a water absorbent intermediate mat 8 is sandwiched between a water absorbent upper sheet 3a and a waterproof lower sheet 9, and a waterproof cushino mat 7 attached to one end (corresponding to the lumbrosacral region) of the base and covered upside with another water absorbent sheet 3. Both side of the base are folded in two layers so that the upper sheet 3a may face upwardly in the folded portions 1a and 1b and also may form a "puddle" 1c for human waste inside the base. Attached to one end of the base is a concave cushion mat 7 matching in shape with the lumbosacral region 2a in the manner that the mat 7 extends over the folded portions 1a and 1b at one end portion of the base.

Since the upper sheets 3a and 3 come in direct contact with the patient's bedding, body and clothes, the sheets 3a and 3 are made of a material excellent in hygroscopicity, air permeability, and durability, such as cotton, gauze, non-woven fabric. The intermediate mat 8 is primarily intended to absorb sweat and urine, and may be constructed of a material excellent in air permeability, such fibrous pulp, soft paper, cotton, and gauze laid in layers and may suitably contain an absorbent such as absorbent polymer.

Figure 5:
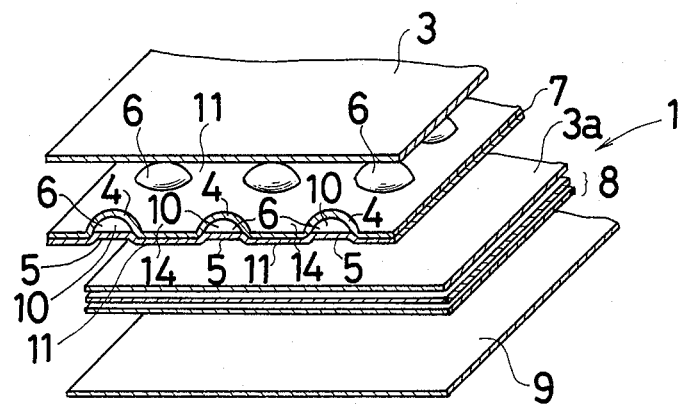
FIG. 5 is an exploded perspective view showing the details of the construction of a raised portion of the bedsore-free diaper in FIG. 1.
Figure 6:
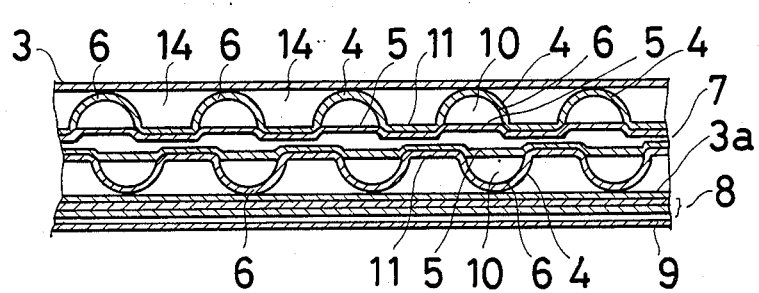
FIG. 6 is a sectional view showing the case wherein the waterproof cushion mat of the bedsore-free diaper is bent or folded back.

The waterproof cushion mat 7, as shown in FIGS. 5 and 6, consists of two upper and lower films 4 and 5 made of soft polyethylene or other soft waterproof material, a plurality of pneumatically distended portions 6... expanded by the air 10 sealed between the films 4 and 5 and arranged regularly and independently at intervals from each other with respect to the surface direction of the respective films 4 and 5, and the films in the portions other than the distended portions 6... are vertically heat sealed to define a flat portion 11. The waterproof cushion mat 7 shown is of a soft polyethylene product commercially available under the trade name "AIR CAP" (manufactured by Ube Kosan K.K.) and the distended portions 6... each are of semispherical shape about 10 mm in diameter and are arranged regularly in checkerboard fashion at small intervals from one another with respect to the surface direction of the films 4 and 5. It is to be understood that the shape and arrangment of the distended portions 6 ... should not be limited to those described above.

Because the lower sheet 9 raises a fear of the bed surface being moistened by the diaper containing heavy moisture due to urine, a waterproof material such polyethylene film, vinyl film is used. Accordingly, in the folded portions 1a and 1b on both sides of the sheet 9, the sheet 9 in the folded portion 1a and 1b is spottily heat sealed to each other so as to hold the sheet 9 folded in two.

In the case of FIG. 5, the cushion mat 7 is used in a single sheet, and is sandwiched between the sheet 3 and 3a in the manner that the distended portions 6 ... face toward the body side. This embodiment is suitable for the case wherein the distended portions 6 ... are large enough in diameter to make ti unnecessary to fold the sheet in two upper and lower layers (double) as in another embodiment in FIG. 6. The laminated structure in FIG. 6 is suitable for the case wherein it is used as a bedsore-free mat for use in the regions such as the nape, elbow, and heel which are likely to produce little moisture.

In a "puddle" for urine of the upper sheet 3a, a guide mark M adapted to correspond to the anus of the human body is printed on the center line of the sheet 3a in the longitudinal direction thereof at a specified space, of say, 8 cm from one end of the cushion mat 7 and is designed to make it possible for the mat 7 to be applied to the lumbosacral region adequately.

Figure 2:
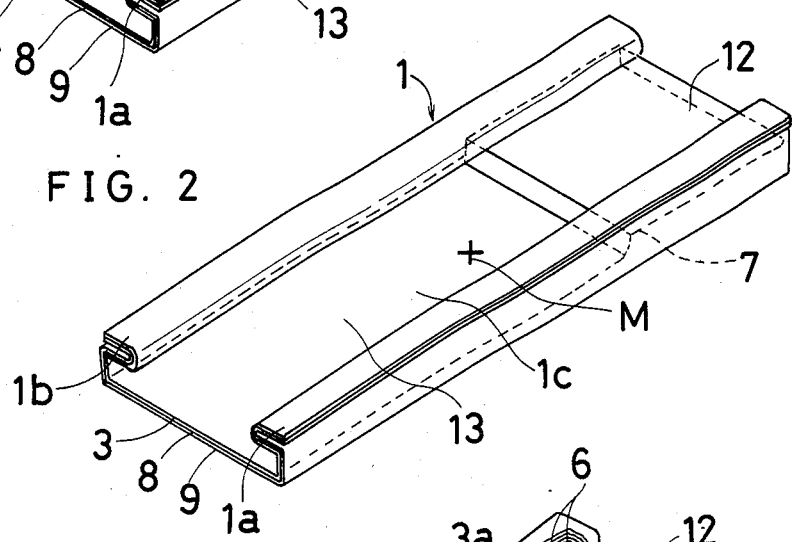
FIG. 2 is a perspective view showing another embodiment of a bedsore-free diaper of the invention.
Figure 3:
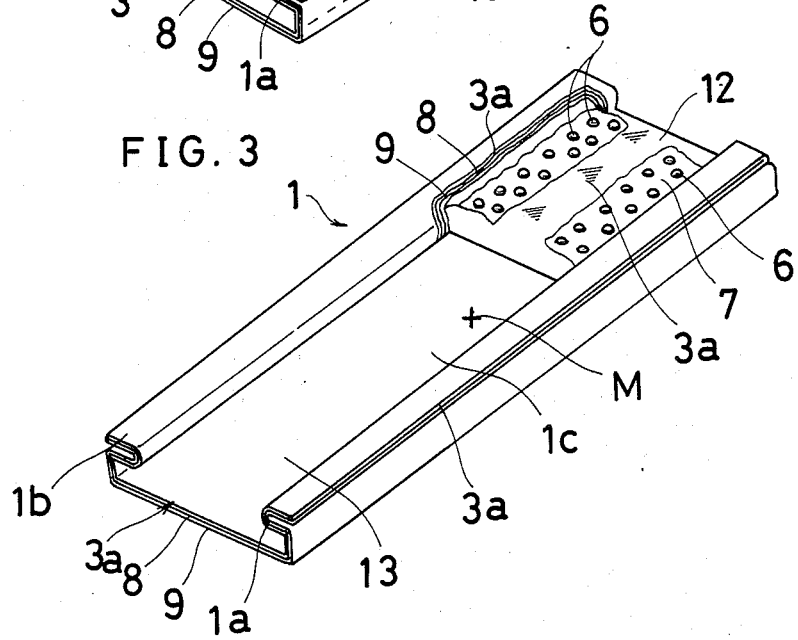
FIG. 3 is a perspective view, broken in part, of FIG. 2.
Figure 4:
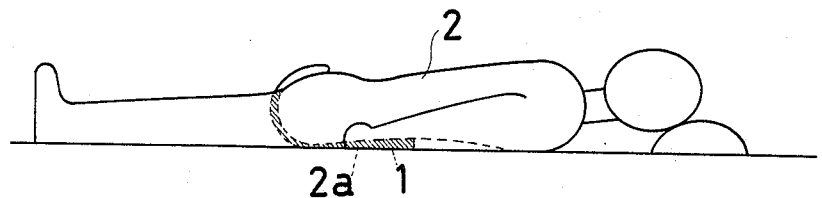
FIG. 4 is a side view explaining a mode of use of the bedsore-free diaper of the invention.

The bedsore-free diaper 1 in FIGS. 2 and 3 showin the second embodiment is a modification of the first embodiment so designed as the cushion mat 7 is concealedly embedded in the diaper, i.e. at one end of the diaper 1, the waterproof cushion mat 7 is inserted between the upper sheet 3a and the intermediate mat 8 inside both sides of the diaper so that the water absorbent sheet 3 to be laminated on the mat 7 can be dispensed with and also the taks of straddling the cushion mat 7 to one end of the base as in the first embodiment is omitted. The second embodiment is the same as the first one except that the former is different in the manner of attachment of the cushion mat 7 from the latter.

In FIGS. 1 to 6, the water absorbent sheets 3 and 8 are laid in multiple layers to form a base of the diaper 1 to absorbe and receive sweat and human waste of the patient 2.

Particularly, the folded portions 1a and 1b are formed with a pocket 1c for "puddle" by both side portions being folded in two so as to provide improved receptive capacity for human waster to thereby prevent lateral flow of the human waste to prevent lateral flow of the human waste. Furthermore, because the waterproof cushion mat 7 to be applied to the lumbosacral region 2a of a person heavy in body weight is attached so as to face the distended portions 6 ... toward the user's body, the mat 7 supports the body weight spottily (by nonsurface contact) by the pneumatically distended portions 6 ... to thereby make it difficult to cause incomplete circulation of the blood through the skin and make it possible for the distended portions 6 to respond to the body weight by the elastic deformation of the portions 6 ..., so that not only a soft sense of contact is obtained but also mere slight movement of the body can displace the position of the mat 7 in pressing contact with the skin into a new position each time the patient's body is moved, with the result that the diaper of the invention provides more agreeable feeling on than that of the conventional fixed contact type. The air existing in the flat portions 14 between the distended portions 6 of the cushion mat 7 allows the mat 7 to keep adequate air permeability even in the state of its supporting the body weight, so that not only development of moisture in the portion of the body in contact with the diaper due to sweat and the moisture in the atmosphere is reduced but also heat insulation is obtained by the air 10 inside the distended portions 6. The mat 7 itself is waterproof, and accordingly, even if the underside of the mat 7 gets moistened (for example, the bed gets wet), the mat prevents the moisture from shifting upwardly to the upside of the mat 7. The lumbosacral region rests on the raised portion 12 of the cushion mat 7, but because the portion 12 is higher by the thickness of the mat 7 than other skirt portion 13, moisture as the human waste flows from the raised portion 12 to the skirt portion 13 and thereafter is absorbed by the intermediate mat 8 consisting of the water absorbent sheet in the intermediate portion. The water resistance of the cushion mat 7 prevents the moisture from reaching the patient's body. Also, because the lower sheet 9 uses a waterproof sheet, the moisture does not reach the bed. Because the cushion mat 7 shown in FIG. 6 is folded in two and the pneumatically distended portions 6 ... are arranged on the upper and lower sides in substantially opposed relation with each other, they are increased in resistance to bedsores and in air permeation in a greater degree, and also because spaces in the distended portions arranged in the downward direction are maintained even under load, they are higher in moisture holding capacity than the conventional pneumatically distended portions whereby the lumbosacral region is assured of a very comfortable sense of lying in bed and cleanliness and is protected against the formation of bedsores.

The guide mark M printed on the cushion mat 7 on substantially the center line of the mat in the longitudinal direction thereof at specified intervals from the waterproof cushion 7 is an indication mark for placing the diaper under the patient 2 in the manner that the mark M may be positioned immediately under the anus, and when the cushion mat 7 is applied adequately to the lumbosacral region 2a by virtue of the mark M, deflection of the diaper 1 from the right position can be prevented and thus the mat 7 is protected against its contamination caused by the deflection of the diaper 1.

As described above, the bedsore-free diaper 1 of the invention can provide the advantage that, by placing the diaper 1 under the patient's body so as to position the guide mark M under the anus, the waterproof cushion mat 7 is held to the lumbosacral region which supports a greater part of the weight of the bedridden patient 2 confined to his bed for a long time and in which bedsores most often form and that the folded portions 1a and 1b on both sides of the diaper not only effectively prevents lateral leak of human waste out of the diaper and extends to the bedridden patient a great benefit in the form of freedom of bedsores unobtainable fro the use of conventional diapers but also relieves those attending on invalids of their trouble to frequently change the invalid's positions in bed and their wet sheets.

I claim:

1. A bedsore-free diaper characterized in that, a diaper formed of water absorbent sheets laid in lyers, said bedsore-free diaper comprises:

folded portions for preventing lateral leakage of human waste out of the diaper, said folded portions being disposed at both sides of said diaper with said folded portions directed upwardly;

a water absorbent cushion mat including a plurality of pneumatically distended portions, said portions being provided independently of each other inside said diaper in such a manner that said distended portions face the side in contact with the human body so as to correspond with the lumbosacral region of the human body inside said diaper; and a guide mark provided inside said diaper on substantially a center line in the longitudinal direction of said diaper at specified interval from said cushion mat, said mark being intended to provide an indication mark by which the user can precisely apply said cushion mat to the lumbosacral region.

2. A diaper according to claim 1 wherein said guide mark is disposed in corresponding relation with the position of anus of the human body.

3. A diaper according to claim 1 wherein said waterproof cushion mat is folded in two upper and lower layers in a manner that the pneumatically distended portions of said mat may lie on the outside of the mat.

4. A diaper according to claim 1 wherein said waterproof cushion mat is laid over both folded portions of said diaper.

5. A diaper according to claim 1 wherein said diaper is formed of a lowermost waterproof sheet, an intermediate mat and an uppermost water absorbent sheet laid in layers.

6. A diaper according to claim 5 wherein said waterproof mat is interposed between said uppermost water absorbent sheet and said intermediate mat of said diaper.

7. A diaper according claim 5 wherein said diaper is folded in two on both sides in a manner such that the upper surface of said uppermost water absorbent sheet of said diaper may extend upwardly and such that the waterproof sheet forming the lowermost layer is spot heat sealed in said two-folded portion.

8. A diaper according to claim 1, or 2 or 3 or 4 wherein said waterproof cushion mat comprises two upper and lower films made of a soft polyethylene or other soft waterproof material and a plurality of pneumatically distended portions, said portions being expanded between said upper and lower films by air sealed between the films and being arranged regularly and independtly at internal from each other with respect to a surface direction of each of the films.

* * * * *

UNITED STATES PATENT AND TRADEMARK OFFICE
CERTIFICATE OF CORRECTION

PATENT NO. : 4,610,679
DATED : September 9, 1986
INVENTOR(S) : Masao Matsushita

It is certified that error appears in the above—identified patent and that said Letters Patent is hereby corrected as shown below:

Title page:

At [30] Foreign Application Priority Data change "5037669[U]" to --60-37669[U]--.

Signed and Sealed this

Eighteenth Day of November, 1986

Attest:

DONALD J. QUIGG

*Attesting Officer*   *Commissioner of Patents and Trademarks*